United States Patent
Biba et al.

(10) Patent No.: US 7,563,807 B2
(45) Date of Patent: Jul. 21, 2009

(54) REMOVAL OF ALDEHYDE IMPURITY BY REACTIVE POLYSTYRENE RESINI

(75) Inventors: Mirlinda Biba, Piscataway, NJ (US); Paul Compton Collins, Bridgewater, NJ (US); Christopher Joseph Welch, Cranbury, NJ (US); David A. Conlon, Plainsboro, NJ (US); Antoinette Drahus, Lexington, MA (US)

(73) Assignee: Merck & Co. Inc., Rahway, NJ (US)

( * ) Notice: Subject to any disclaimer, the term of this patent is extended or adjusted under 35 U.S.C. 154(b) by 650 days.

(21) Appl. No.: 10/526,782

(22) PCT Filed: Sep. 12, 2003

(86) PCT No.: PCT/US03/28716

§ 371 (c)(1), (2), (4) Date: Mar. 4, 2005

(87) PCT Pub. No.: WO2004/026794

PCT Pub. Date: Apr. 1, 2004

(65) Prior Publication Data

US 2007/0054941 A1    Mar. 8, 2007

Related U.S. Application Data

(60) Provisional application No. 60/411,245, filed on Sep. 17, 2002.

(51) Int. Cl.
  *A61K 31/47* (2006.01)
  *A61K 31/4709* (2006.01)
  *C07D 215/14* (2006.01)
  *C07D 401/10* (2006.01)
  *C07D 413/10* (2006.01)

(52) U.S. Cl. .................. 514/314; 514/311; 514/256; 514/253.06; 546/167; 546/172; 546/73

(58) Field of Classification Search ............ 514/253.06, 514/256, 311, 314; 546/167, 172, 173
See application file for complete search history.

(56) References Cited

U.S. PATENT DOCUMENTS 6,410,563 B1    6/2002    Deschenes et al.

FOREIGN PATENT DOCUMENTS

WO    WO-03/02118 A1 *    1/2003

* cited by examiner

*Primary Examiner*—Kamal Saeed
*Assistant Examiner*—Janet L Coppins
(74) *Attorney, Agent, or Firm*—Sylvia A. Ayler; William Krovatin

(57) ABSTRACT

A purification method in the preparation of a substituted 8-arylquinoline, wherein the aryl group at the 8-position contains a substituent substituted-alkenyl group, utilizes a polystyrene-based sulfonylhydrazine reactive resin to remove an aldehyde impurity.

7 Claims, No Drawings

REMOVAL OF ALDEHYDE IMPURITY BY REACTIVE POLYSTYRENE RESINI

CROSS REFERENCE TO RELATED APPLICATIONS

This application is a U.S. National Phase application under 35 U.S.C. § 371 of PCT Application No. PCT/US2003/028716, filed Sep. 12, 2003, which claims priority under 35 U.S.C. 119 to U.S. No. 60/411,245, filed Sep. 17, 2002.

BACKGROUND OF THE INVENTION

1. Field of the Invention

The present invention is directed to a method of selectively removing an aldehyde impurity from a process stream in the preparation of a substituted 8-arylquinoline. In particular, this invention is directed to a method of utilizing a polystyrene-based sulfonylhydrazine reactive resin to remove an aldehyde impurity in the preparation of a substituted 8-arylquinoline wherein the aryl group at the 8-position contains a substituent substituted-alkenyl group.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3',5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3',5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

International Patent Publication WO9422852 describes quinolines as PDE4 inhibitors. U.S. Pat. No. 6,410,563 describes substituted 8-arylquinolines as PDE4 inhibitors.

However, there remains a need for methods to make such novel compounds without undesirable impurities.

SUMMARY OF TH INVENTION

The present invention is directed to a purification method in the preparation of a substituted 8-arylquinoline, wherein the aryl group at the 8-position contains a substituent substituted-alkenyl group, that utilizes a polystyrene-based sulfonylhydrazine reactive resin to remove an aldehyde impurity.

DETAILED DESCRIPTION OF THE INVENTION

A method of this invention forms a solution of a compound represented by Formula (I):

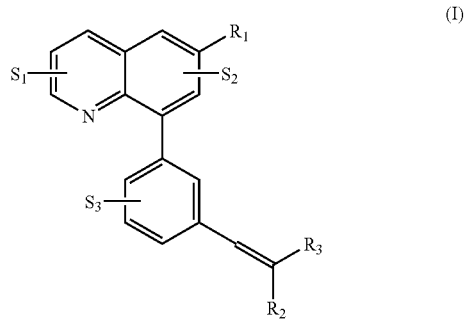

substantially free of the aldehyde represented by Formula (II):

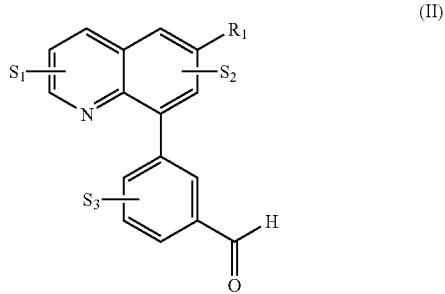

wherein $S_1$, $S_2$, and $S_3$ are independently H, —OH, halogen, —$C_1$-$C_6$alkyl, —$NO_2$, —CN, or —$C_1$-$C_6$alkoxy, wherein the alkyl and alkoxy groups are optionally substituted with 1-5 substituents; wherein each substituent is independently a halogen or OH;

$R_1$ is a H, OH, halogen, carbonyl, or —$C_1$-$C_6$alkyl, -cycloC$_3$-$C_6$alkyl, —$C_1$-$C_6$alkenyl, —$C_1$-$C_6$alkoxy, aryl, heteroaryl, —CN, -heterocycloC$_3$-$C_6$alkyl, -amino, —$C_1$-$C_6$alkylamino, —($C_1$-$C_6$alkyl)($C_1$-$C_6$alkyl)amino, —$C_1$-$C_6$alkyl(oxy)$C_1$-$C_6$alkyl, —C(O)NH(aryl), —C(O)NH(heteroaryl), —SO$_n$NH(aryl), —SO$_n$NH(heteroaryl), —SO$_n$NH($C_1$-$C_6$alkyl), —C(O)N($C_0$-$C_6$alkyl)($C_0$-$C_6$alkyl), —NH—SO$_n$—($C_1$-$C_6$alkyl), —SO$_n$—($C_1$-$C_6$alkyl), —($C_1$-$C_6$alkyl)—O—C(CN)-dialkylamino, or —($C_1$-$C_6$alkyl)—SO$_n$—($C_1$-$C_6$alkyl) group, wherein any of the groups is optionally substituted with 1-5 substituents; wherein each substituent is independently a halogen, —OH, —CN, —$C_1$-$C_6$alkyl, -cycloC$_3$-$C_6$alkyl, —C(O)(heterocycloC$_3$-$C_6$alkyl), —C(O)—O—($C_0$-$C_6$alkyl), —C(O)-aryloxy, —$C_1$-$C_6$alkoxy, —($C_0$-$C_6$alkyl)($C_0$-$C_6$alkyl)amino, cycloalkyloxy, acyl, acyloxy, -cycloC$_3$-$C_6$alkyl, heterocycloC$_3$-$C_6$alkyl, aryl, heteroaryl, carbonyl, carbamoyl, or —SO$_n$—($C_1$-$C_6$alkyl);

$R_2$ and $R_3$ independently is an aryl, heteroaryl, H, halogen, —CN, —$C_1$-$C_6$alkyl, heterocycloC$_{3-6}$alkyl, —$C_1$-$C_6$alkoxy, carbonyl, carbamoyl, —C(O)OH, —($C_1$-$C_6$alkyl)—SO$_n$—

($C_1$-$C_6$alkyl), —C(O)N($C_0$-$C_6$alkyl)($C_0$-$C_6$alkyl), or —$C_1$-$C_6$alkylacylamino group, wherein any of the groups is optionally substituted with 1-5 substituents, wherein each substituent is independently an aryl, heteroaryl, halogen, —$NO_2$, —C(O)OH, carbonyl, —CN, —$C_1$-$C_6$alkyl, —$SO_n$—($C_1$-$C_6$alkyl), —$SO_n$—(aryl), aryloxy, -heteroaryloxy, $C_1$-$C_6$alkoxy, N-oxide, —C(O)-heterocyclo$C_3$-$C_6$alkyl, —NH-cyclo$C_3$-$C_6$alkyl, amino, —OH, or —($C_0$-$C_6$alkyl)($C_0$-$C_6$alkyl)amino, —C(O)—N($C_0$-$C_6$alkyl)($C_0$-$C_6$alkyl) substituent group, wherein each substituent group independently is optionally substituted with —OH, $C_1$-$C_6$alkoxy, —$C_1$-$C_6$alkyl, -cyclo$C_3$-$C_6$alkyl, aryloxy, —C(O)OH, —C(O)O($C_1$-$C_6$alkyl), halogen, —$NO_2$, —CN, —$SO_n$—($C_1$-$C_6$alkyl), or —C(O)—N($C_0$-$C_6$alkyl)($C_0$-$C_6$alkyl);

one of $R_2$ and $R_3$ must be an aryl or heteroaryl, optionally substituted;

n is independently 0, 1, or 2;

said method comprises the step of contacting a dimethylformamide solution of the compound represented by Formula (I) with a polystyrene-based sulfonylhydrazine reactive resin effective to substantially remove the aldehyde represented by Formula (II). The solution can be any convenient nonaqueous solution such as, for example, a DMF solution. The reagent resin is any convenient hydrazine resin such as, for example, a polystyrene-based suylfonylhydrazine reactive resin or any similar solid material bearing pendant hydrazine moeties.

The compound represented by Formula (I) can then be crystallized by the addition of an antisolvent to yield crystalline compound represented by Formula (I) substantially free of the aldehyde impurity represented by Formula (II).

In one embodiment, the method of this invention forms a solution of a compound represented by Formula (Ia):

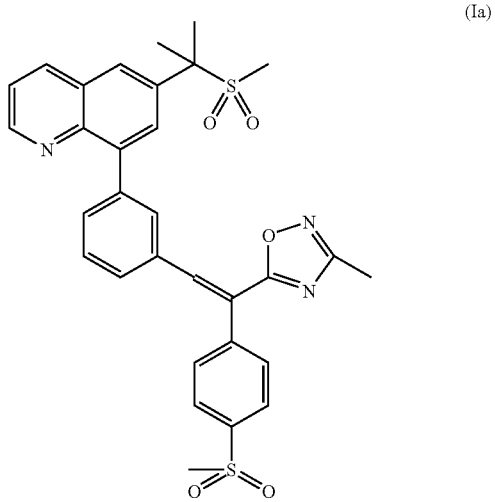

(Ia)

substantially free of the aldehyde represented by Formula (IIa):

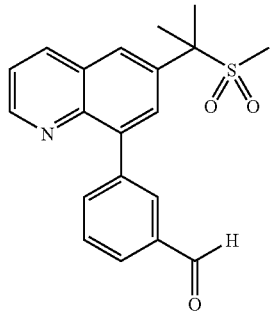

(IIa)

said method comprises the step of contacting a solution of the compound represented by Formula (Ia) with a polystyrene-based sulfonylhydrazine reactive resin effective to substantially remove the aldehyde represented by Formula (IIa).

The compound represented by Formula (Ia) can then be crystallized by the addition of an antisolvent to yield crystalline compound represented by Formula (I) substantially free of the aldehyde impurity represented by Formula (IIa). The purification treatment would work for various salts or for the free base. The salt can be conveniently, for example, the besylate salt.

"Substantially free" means that the aldehyde impurity is present at levels less than 0.075% by weight. The aldehyde impurity typically is present after the final chemical reaction step at a low level of amount 0.5% by weight. This solution is called the untreated solution. The untreated solution is then subject to a sulfonylhydrazine resin such as, for example, that available from Argonaut Technologies (Foster City, Calif.) at a convenient treatment level such as, for example, about 20 mg resin for each gram of product. The untreated solution can be highly concentrated in product such as, for example, 300 mg/mL.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

Ther term "$C_0$-$C_6$alkyl" includes alkyls containing 6, 5, 4, 3, 2, 1, or no carbon atoms. An alkyl with no carbon atoms is a hydrogen atom substituent or a direct bond—depending on whether the alkyl is a terminus or a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocyclo$C_{3-7}$alkyl include, for example, azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

Examples of aryl($C_{1-6}$)alkyl include, for example, phenyl($C_{1-6}$)alkyl, and naphthyl($C_{1-6}$)alkyl.

Examples of heterocyclo$C_{3-7}$alkylcarbonyl($C_{1-6}$)alkyl include, for example, azetidinyl carbonyl($C_{1-6}$)alkyl, pyrrolidinyl carbonyl($C_{1-6}$)alkyl, piperidinyl carbonyl($C_{1-6}$)alkyl, piperazinyl carbonyl($C_{1-6}$)alkyl, morpholinyl carbonyl($C_{1-6}$)alkyl, and thiomorpholinyl carbonyl($C_{1-6}$)alkyl.

The term "amine" unless specifically stated otherwise includes primary, secondary and tertiary amines.

Unless otherwise stated, the term "carbamoyl" is used to include —NHC(O)O$C_1$-$C_4$alkyl, and —OC(O)NH$C_1$-$C_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$)alkyl includes substitution on the aryl group as well as substitution on the alkyl group.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are benzenesulfonic, citric, hydrobromic, hydrochloric, maleic, phosphoric, sulfuric, and tartaric acids.

The abbreviations used herein have the following tabulated meanings. Abbreviations not tabulated below have their meanings as commonly used unless specifically stated otherwise.

| | |
|---|---|
| Ac = | acetyl |
| Bn = | benzyl |
| CAMP | cyclic adenosine-3',5'-monophosphate |
| DBU = | 1,8-diazabicyclo[5.4.0]undec-7-ene |
| DIBAL = | diisobutylaluminum hydride |
| DMAP = | 4-(dimethylamino)pyridine |

-continued

| | |
|---|---|
| DMF = | N,N-dimethylformamide |
| Et$_3$N = | triethylamine |
| GST | glutathione transferase |
| HMDS | hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt 6H$_2$O |
| Ms = | methanesulfonyl = mesyl = SO$_2$Me |
| Ms0 = | methanesulfonate = mesylate |
| NSAID = | non-steroidal anti-inflammatory drug |
| o-Tol = | ortho-tolyl |
| OXONE ® = | 2KHSO$_5$•KHSO$_4$•K$_2$SO$_4$ |
| PCC = | pyridinium chlorochromate |
| PDC = | pyridinium dichromate |
| PDE | phosphodiesterase |
| Ph = | phenyl |
| Phe = | benzenediyl |
| PMB = | para-methoxybenzyl |
| Pye = | pyridinediyl |
| r.t. = | room temperature |
| Rac. = | racemic |
| SAM = | aminosulfonyl or sulfonamide or SO$_2$NH$_2$ |
| SEM = | 2-(trimethylsilyl)ethoxymethoxy |
| SPA = | scintillation proximity assay |
| TBAF = | tetra-n-butylammonium fluoride |
| Th = | 2-or 3-thienyl |
| TFA = | trifluoroacetic acid |
| TFAA = | trifluoroacetic acid anhydride |
| THF = | tetrahydrofuran |
| Thi = | thiophenediyl |
| TLC = | thin layer chromatography |
| TMS-CN = | trimethylsilyl cyanide |
| TMSI | trimethylsilyl iodide |
| Tz = | 1H (or 2H)-tetrazol-5-yl |
| CAN | ceric ammonium nitrate |
| C$_3$H$_5$ = | allyl |

ALKYL GROUP ABBREVIATIONS

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

EXAMPLES

The present invention include the following methods. The substituents are the same as in Formula (I) except where defined otherwise.

Removal of the aldehyde impurity (IIa) using a reactive polystyrene-based sulfonylhydrazine resin. Sulfonylhydrazine resin (polystyrene-based tosylhydrazine resin (PS-TsNHNH$_2$, Argonaut Technologies, Inc., Foster City, Calif.) was pre-washed by slurrying 70 mg resin in 5 mL DMF at rt for 20 min, then decanting the supernatant solution. Following a second washing and decanting, 12 mL of DMF, 3.0 g of crude Ia as the free base and 0.85 g of benzenesulfonic acid were added to the washed resin. The slurry was allowed to age for one hour at ambient temperature with stirring. Resin was removed by vacuum filtration to afford a clear yellow solution. The resin was rinsed with 3 mL of DMF and the rinse added to the reaction solution. The product (Ia) was crystallized by addition of 63 mL of isopropyl acetate at rt followed by cooling to 5° C. and aging 12 hours. The resulting crystals were isolated by vacuum filtration and washed with 2*15 mL of 95:5 IPAc:DMF. HPLC analysis on the isolated product revealed 86% removal of the aldehyde impurity (IIa). No impurity rejection was observed without resin treatment. The mother liquor losses were similar to the process without resin treatment and no new impurities were seen by HPLC.

Other variations or modifications, which will be obvious to those skilled in the art, are within the scope and teachings of this invention. This invention is not to be limited except as set forth in the following claims.

What is claimed is:

1. A method of forming a clean solution of a compound represented by Formula (I):

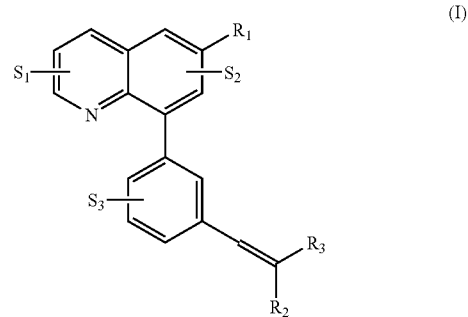

said clean solution being substantially free of an aldehyde represented by Formula (II):

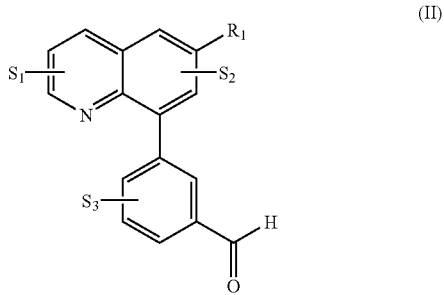

wherein
$S_1$, $S_2$, and $S_3$ are independently H, —OH, halogen, —C$_1$-C$_6$alkyl, —NO$_2$, —CN, or —C$_1$-C$_6$alkoxy, wherein the alkyl and alkoxy groups are optionally substituted with 1-5 substituents; wherein each substituent is independently a halogen or OH;

$R_1$ is a H, OH, halogen, carbonyl, or —C$_1$-C$_6$alkyl, -cycloC$_3$-C$_6$alkyl, —C$_1$-C$_6$alkenyl, —C$_1$-C$_6$alkoxy, aryl, heteroaryl, —CN,-heterocycloC$_3$-C$_6$alkyl, -amino, —C$_1$-C$_6$alkylamino, —(C$_1$-C$_6$alkyl)(C$_1$-C$_6$alkyl) amino, —C$_1$-C$_6$alkyl(oxy)C$_1$-C$_6$alkyl, —C(O)NH (aryl), —C(O)NH(heteroaryl), —SO$_n$NH(aryl), —SO$_n$NH(heteroaryl), —SO$_n$NH(C$_1$-C$_6$alkyl), —C(O) N(C$_0$-C$_6$alkyl)(C$_0$-C$_6$alkyl), —NH—SO$_n$—(C$_1$-C$_6$alkyl), —SO$_n$—(C$_1$-C$_6$alkyl), —(C$_1$-C$_6$alkyl)—O—C(CN)-dialkylamino, or —(C$_1$-C$_6$alkyl)—SO$_n$—(C$_1$-C$_6$alkyl) group, wherein any of the groups is optionally substituted with 1-5 substituents; wherein each substituent is independently a halogen, —OH, —CN, —C$_1$-C$_6$alkyl, -cycloC$_3$-C$_6$alkyl, —C(O)(heterocycloC$_3$-C$_6$alkyl), —C(O)—O—(C$_0$-C$_6$alkyl), —C(O)-aryloxy, —C$_1$-C$_6$alkoxy, —(C$_0$-C$_6$alkyl)(C$_0$-C$_6$alkyl)amino, cycloalkyloxy, acyl, acyloxy, -cycloC$_3$-C$_6$alkyl, heterocycloC$_3$-C$_6$alkyl, aryl, heteroaryl, carbonyl, carbamoyl, or —SO$_n$—(C$_1$-C$_6$alkyl);

R$_2$ and R$_3$ independently is an aryl, heteroaryl, H, halogen, —CN, —C$_1$-C$_6$alkyl, heterocycloC$_{3-6}$alkyl, —C$_1$-C$_6$alkoxy, carbonyl, carbamoyl, —C(O)OH, —(C$_1$-C$_6$alkyl)—SO$_n$—(C$_1$-C$_6$alkyl), —C(O)N(C$_0$-C$_6$alkyl)(C$_0$-C$_6$alkyl), or —C$_1$-C$_6$alkylacylamino group, wherein any of the groups is optionally substituted with 1-5 substituents, wherein each substituent is independently an aryl, heteroaryl, halogen, —NO$_2$, —C(O)OH, carbonyl, —CN, —C$_1$-C$_6$alkyl, —SO$_n$—(C$_1$-C$_6$alkyl), —SO$_n$—(aryl), aryloxy, -heteroaryloxy, C$_1$-C$_6$alkoxy, N-oxide, —C(O)-heterocycloC$_3$-C$_6$alkyl, —NH-cycloC$_3$-C$_6$alkyl, amino, —OH, or —(C$_0$-C$_6$alkyl)(C$_0$-C$_6$alkyl)amino, —C(O)—N(C$_0$-C$_6$alkyl)(C$_0$-C$_6$alkyl) substituent group, wherein each substituent group independently is optionally substituted with —OH, C$_1$-C$_6$alkoxy, —C$_1$-C$_6$alkyl, -cycloC$_3$-C$_6$alkyl, aryloxy, —C(O)OH, —C(O)O(C$_1$-C$_6$alkyl), halogen, —NO$_2$, —CN, —SO$_n$—(C$_1$-C$_6$alkyl), or —C(O)—N(C$_0$-C$_6$alkyl)(C$_0$-C$_6$alkyl);

one of R$_2$ and R$_3$ must be an aryl or heteroaryl, optionally substituted; and n is independently 0, 1, or 2;

said method comprising:

a step of contacting an untreated solution of the compound represented by Formula (I) with a reactive resin effective to substantially remove the aldehyde represented by Formula (II) from said untreated solution to form the clean solution.

2. The method of claim 1, wherein said solutions are in dimethylformamide.

3. The method of claim 1, wherein said reactive resin is a solid material bearing a pendant hydrazine moety.

4. The method of claim 3 wherein said reactive resin is a polystyrene-based sulfonylhydrazine.

5. The method of claim 1, further comprising a step of:

adding an antisolvent to said clean solution to yield a crystalline compound represented by Formula (I) substantially free of the aldehyde impurity represented by Formula (II).

6. A method of forming a clean solution of a compound represented by Formula (Ia):

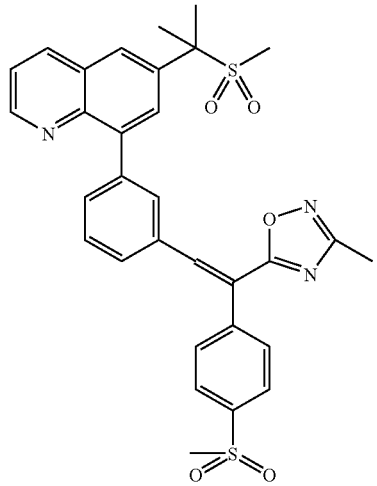

(Ia)

substantially free of an aldehyde represented by Formula (IIa):

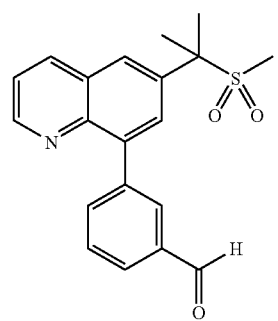

(IIa)

said method comprising the step of contacting an untreated solution of the compound represented by Formula (Ia) with a polystyrene-based sulfonylhydrazine reactive resin effective to substantially remove the aldehyde represented by Formula (IIa) from said untreated solution to form said clean solution.

7. The method of claim 6, further comprising a step of:

adding an antisolvent to said clean solution to yield a crystalline compound represented by Formula (Ia) substantially free of the aldehyde impurity represented by Formula (IIa).

* * * * *